United States Patent [19]
Hawks

[11] Patent Number: 4,943,285
[45] Date of Patent: Jul. 24, 1990

[54] UNDULATING RECTAL SPECULUM

[76] Inventor: Robert A. Hawks, 3602 W. Danbury Dr., Glendale, Ariz. 85308

[21] Appl. No.: 289,566

[22] Filed: Dec. 22, 1988

[51] Int. Cl.$^5$ .............................................. A61M 3/02
[52] U.S. Cl. ...................................... 604/275; 100/29
[58] Field of Search ................ 604/275, 278, 279, 54, 604/164, 170; 128/750; 600/29

[56] References Cited
U.S. PATENT DOCUMENTS 2,458,719  1/1949  McCormick .......................... 604/33
4,325,370  4/1982  Young ................................. 604/275
4,712,536  12/1987  Hawks ................................ 128/750
4,842,580  6/1989  Ouelette ............................ 604/275

*Primary Examiner*—Stephen C. Pellegrino
*Attorney, Agent, or Firm*—Cahill, Sutton & Thomas

[57] ABSTRACT

A rectal speculum for use in conjunction with colonic lavage has an axially undulating exterior surface for defining an annular depression to receive and be gripped by the rectal sphincter muscle upon insertion of the speculum.

9 Claims, 1 Drawing Sheet

U.S. Patent
Jul. 24, 1990
4,943,285
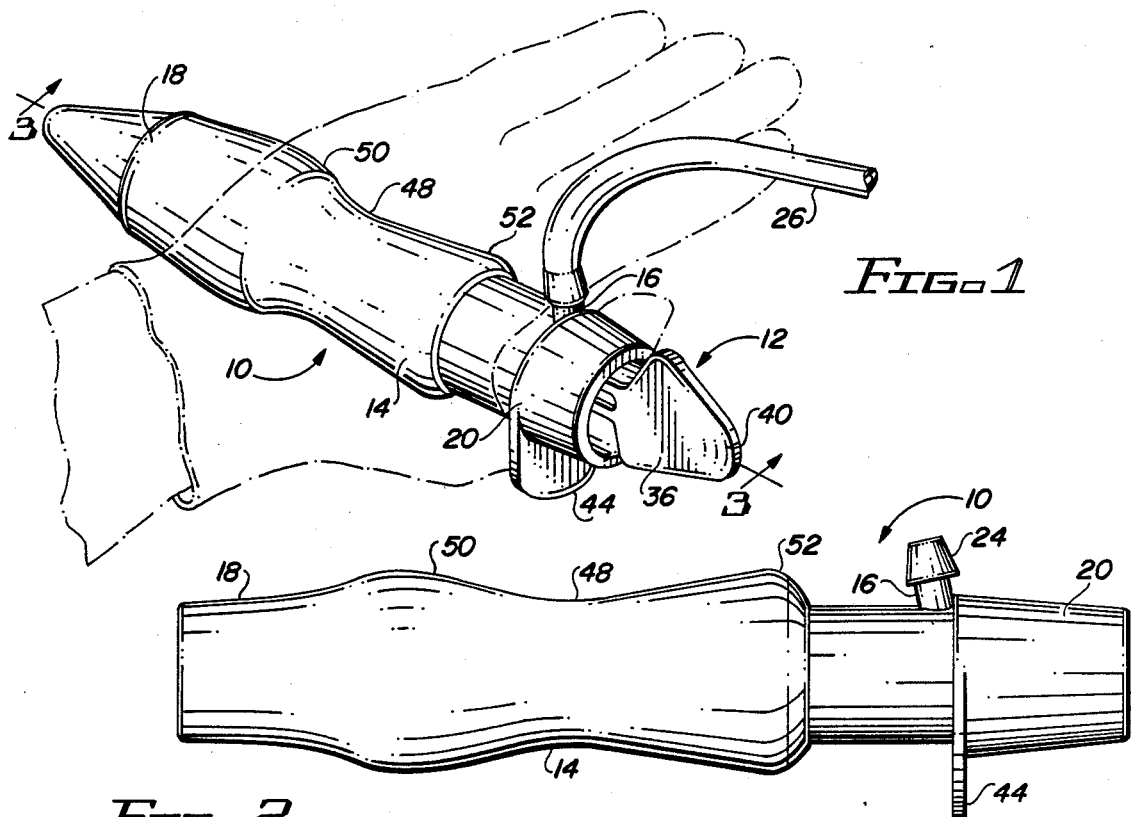
FIG. 1
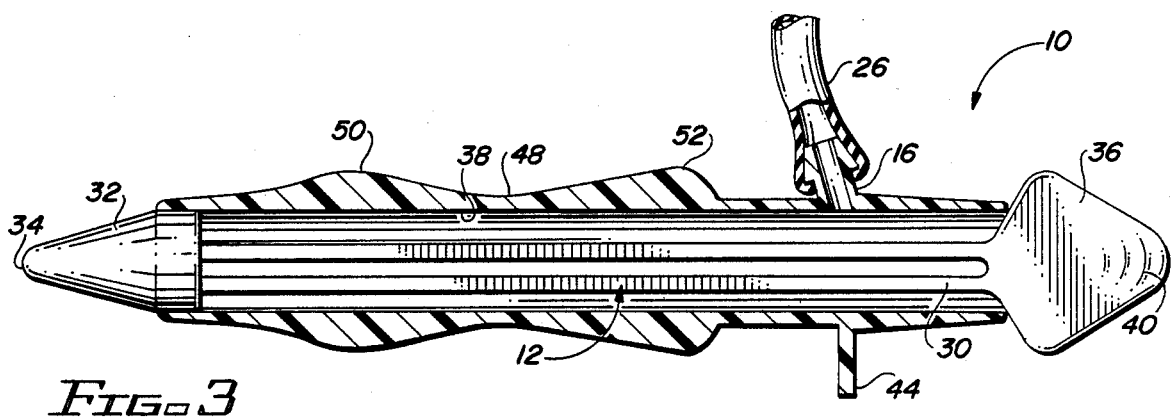
FIG. 2
FIG. 3
FIG. 4

UNDULATING RECTAL SPECULUM

REFERENCE TO RELATED PATENTS

This invention is related to an invention described in U.S. Pat. No. 4,712,536 and directed to an invention by the present inventor.

BACKGROUND OF THE INVENTION

1. Field of the Invention

This invention relates generally to rectal specula and, more particularly, to a speculum for use with a colonic lavage machine.

2. Description of the Prior Art

Devices are known for lavaging the lower intestinal tract of patients suffering from colitis and similar ailments. Examples of such devices can be found in U.S. Pat. Nos. 2,826,197, 3,771,522 and 4,190,059. These devices commonly employ a speculum for directing treating fluids into the patient's colon and subsequently allowing the discharge of fluidized waste matter.

Typically, the rectal specula used with the above devices are formed of a pair of concentric tubes; and inlet tube carries water into the patient's rectum and colon and a discharge tube allows fluidized waste matter to flow out. In order to facilitate insertion of the speculum into the patient's rectal canal, to decrease the patient's discomfort and possible pain and to avoid possible injury to the patient's intestinal tract, the speculum is usually used in combination with an obturator. An obturator typically is an elongated rod having a tapered, cone like portion at one end and a handle portion at the opposite end. The obturator may be inserted through the hollow interior of the speculum from the proximal end to extend the cone like portion from the distal end. The cone like portion facilitates insertion of the speculum. Once the speculum is in place, the obturator is removed by gripping the handle portion and withdrawing it from the speculum.

Conventional specula suffer from a number of drawbacks. In particular, specula having a concentric tube structure are difficult and expensive to manufacture and they are inconvenient to clean and maintain. Furthermore, the process of attaching a discharge hose or conduit to the outlet end of a speculum after removal of an obturator can be painful since the inlet end of the speculum is free to rock or slip in the patient's rectum while the discharge conduit is being attached.

In an attempt to solve the first of these drawbacks, a speculum has been introduced which does away with the conventional concentric tube structure; it is illustrated in U.S. Design Pat. No. D228,204. The Holt speculum includes an unobstructed main tube with a distal end adapted for insertion into a patient's rectum and a proximal end adapted for connection to a waste removal hose; an intersecting inlet tube connectible to a source of water injects water into the main tube. The inlet tube is considerably smaller in diameter than the main tube and is disposed at an acute angle at the discharge end of the main tube. This angle produces a slight fluid flow in the direction of the patient's colon when the lavaging machine is in operation. Once the Holt speculum has been inserted and an associated obturator removed, a waste removal hose must be connected to the proximal end of the tube. Water or other treating fluid flows through the inlet tube to fill up the main tube and waste removal hose until a sufficient back pressure exists to direct the treating fluid into the intestine. When the fluid pressure in the intestine is equal to or greater than the pressure in the main tube and the waste discharge tube, the treating fluid and fluidized waste matter is discharged through the speculum. A drawback of the Holt structure is that the waste matter to be discharged must flow counter to the direction of the fluid flow from the inlet. The resulting pressure on the patient's intestine is relieved more slowly and less effectively than with a speculum in which the waste matter to be discharged does not have to overcome a counter flow. Accordingly, the patient suffers greater pain and discomfort than is necessary. A need therefore exists for a new and improved rectal speculum which overcomes some of the problems and shortcomings of the prior art.

SUMMARY OF THE INVENTION

A speculum has an unobstructed main tube with a distal end adapted to be inserted into a patient's rectum and a proximal end adapted to be connected to a waste removal hose. An inlet tube is connectible to a source of water or other treating fluid to permit injection of the fluid into the main tube. The inlet tube is angled to direct the fluid toward the discharge end of the main tube and assist the fluid flow when the lavaging machine is in operation. An obturator facilitates insertion of the speculum into the patient's rectal canal and lower intestine. To assist in keeping the speculum steady while the obturator is removed and a waste removal hose is attached to the discharge end of the main tube, a thumb rest extends from the speculum. The thumb rest includes a flange extending radially from the outer surface of the main tube and approximately diametrically opposed to the point of intersection between the main tube and the inlet tube. When removing the obturator from the speculum and attaching the waste removal hose, a technician or physician can grasp the speculum between his or her thumb and index finger and place the distal side of the thumb rest against the back of his or her thumb. The resulting steadying force exerted by the hand resists movement of the speculum during removal of the obturator and attachment of the waste removal hose. The speculum is thereby restrained from rocking or moving in the patient's rectal canal and the likelihood of pain, discomfort and injury are decreased. To assist in retaining the speculum in place during use, an annular depression extends about the speculum for receiving the normally contracted rectal sphincter muscle. Annular expansions on opposed sides of the annular depression tend to prevent axial translation of the speculum as a result of interference with the rectal sphincter muscle.

A primary object of the present invention is to provide a rectal speculum retained in place by the normal involuntary contraction of the rectal sphincter muscle.

Another object of the present invention is to provide a guard against inadvertent expulsion of a rectal speculum during use.

Yet another object of the present invention is to provide an easily insertable rectal speculum.

Still another object of the present invention is to provide a rectal speculum having an axially undulating exterior surface.

A further object of the present invention is to provide a method for retaining by contraction of a patient's muscle a rectal speculum in place during use.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a perspective view of a rectal speculum and obturator held in place by a technician or physician prior to use;

FIG. 2 is a side view of the rectal speculum;

FIG. 3 is a cross sectional view of the rectal speculum with an obturator disposed therein and taken along lines 3—3, as shown in FIG. 1; and FIG. 4 is a cross sectional view similar to FIG. 3 after the obturator has been removed.

DESCRIPTION OF THE PREFERRED EMBODIMENT

Referring particularly to FIG. 1, a speculum 10 combined with an obturator 12 is held between the thumb and index finger of the hand of a technician or physician in a manner allowing the obturator to be easily axially withdrawn from the speculum without causing uncomfortable rocking or other movement of the speculum causing uncomfortable rocking or other movement of the speculum placed in a patient's rectum (not shown). As also shown in FIG. 2, the speculum includes a main tube 14 and a smaller diameter inlet tube 16. The main tube includes an intake or distal end 18 adapted for insertion into a patient's rectum (not shown) and a discharge or proximal end 20 adapted for connection to a waste discharge hose 22 (shown in FIG. 4). Preferably, proximal end 20 is a tapered cylinder having a maximum diameter greater than the inner diameter of the waste discharge hose to achieve a tight fit therebetween. The minimum diameter of proximal end 20 may be equal to or less than the diameter of the discharge hose to facilitate sliding of the discharge hose onto the proximal end. Distal end 18 may have a rounded edge for reasons of comfort and safety during insertion of the speculum.

Inlet tube 16 located proximate proximal end 20 forms an obtuse angle with respect to the longitudinal axis of main tube 14 to direct any fluid injected through the inlet tube toward the proximal end. The resulting flow direction causes a slight current in the discharge direction and facilitates removal of fluidized waste matter from the patient's colon when the colonic lavage machine (not shown) is in operation. Preferably, inlet tube 16 includes an annular bead 24 forming a fitting for receiving an inlet tubing or hose 26 connected to a source of treated fluids (not shown) in the lavage machine.

As shown in FIGS. 1 and 3, obturator 12 used in combination with speculum 10 includes an elongated rod 30 having a tapered cone 32 with a rounded tip 34 at the distal end and a handle 36 at the proximal end. Normally, the obturator is inserted from the proximal end of main tube 14 through hollow interior 38 to extend through distal ehnd 18 and facilitate insertion of the speculum into the patient's rectum. Once the speculum has been properly positioned, the obturator is removed from the speculum by pulling on handle 36. The handle may be provided with a plurality of ridges 40 to prevent slipping of the hold on the handle.

To help prevent rocking or other painful movement of speculum 10 when it is within a patient's rectum while the discharge end of main tube 14 is being handled during removal of obturator 12 and during attachment of the waste removal hose 22, a thumb rest 44 extends from main tube 14. The thumb rest may be formed as a flange, as shown, which extends from approximately diametrically opposite the point of intersection between main tube 14 and inlet tube 16. This location ensures that when speculum 10 is held in the position illustrated in FIG. 1, the back of the technician's thumb rests against the distal side of the thumb rest, the knuckle of the index finger bears against the inlet tube and the palm of the hand can rest on the patient's posterior. Upon removal of obturator 12 and attachment of waste removal hose 22, the steadying force exerted by the technician's hand will stabilize and counteract any movement of the speculum which might cause unnecessary pain, discomfort or injury.

After the insertion of the speculum, the normal rhythmic muscular contractions attendant the large intestine, whether voluntary or involuntary, may result in expulsion of the speculum. Such expulsion during use would cause a great deal of discomfort and embarrassment, if not pain or injury. It is well accepted that the rectal sphincter muscle is normally in a contracted state. Moreover, the force exerted by this muscle is relatively substantial. To take advantage of this attribute, main tube 14 includes an axially undulating exterior surface defining an annular depression 48 intermediate a pair of annular expansions 50, 52, as particularly shown in FIG. 4. By inserting speculum 10 to an extent sufficient to place annular depression 48 coincident with the rectal sphincter muscle, the muscle will tend to grip the speculum. As a result of the normally contracted state of the rectal sphincter muscle, it will tend to resist axial translation of the speculum as such translation would cause either of annular expansions 50 or 52 to force the rectal sphincter muscle to extend. Accordingly, once inserted, the speculum would tend to remain in place by the normal reaction of the patient's rectal sphincter muscle.

To assist in insertion of the speculum and minimize discomfort to the patient, the distal side of annular expansion 50 may be very gradual. To obtain assistance of the rectal sphincter muscle in preventing an unnecessary degree of insertion of the speculum, annular expansion 52 may be diametrically increased over that of annular expansion 50; additionally the taper of the distal side of annular expansion 52 may be relatively severe. It is to be noted that the combination of annular depression 48 and annular expansions 50, 52 may be of benefit in providing a more effective seal between the large intestine and the speculum than would a constant diameter speculum.

While interior passage 38 is shown in FIG. 4 as being cylindrical, it may be radially undulating in conformance with the exterior surface of the speculum.

Speculum 10 and obturator 12 are preferably both constructed from an inexpensive, light weight material such as polypropylene or other synthetic resin in order to permit disposal after a single use. However, a reusable, easily cleaned version of the speculum and obturator could also be made from a material such as stainless steel or other suitable metals.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

I claim:

1. A rectal speculum for use with a colonic lavage machine, said speculum comprising in combination:
   (a) a hollow main tube, said main tube including a distal end for insertion into a patient's rectum and a proximal end for connection to a waste discharge hose;
   (b) an axially undulating exterior surface having an annular depression intermediate a pair of annular expansions and disposed about at least an axial length of said main tube for circumscribingly receiving and being gripped by the rectal sphincter muscle of a patient undergoing clonic lavage, one of said pair of annular expansions extending posteriorly from the anterior end of said main tube and having an increasing rate of annular expansion to define a truncated cone with a concave surface extending posteriorly from the anterior end of said main tube to the approximate apex of said one annular expansion, said one annular expansion having a decreasing rate of annular contraction posteriorly from the approximate apex to define a truncated cone with a concave surface extending posteriorly from the approximate apex of said one annular expansion to the approximate midpoint of said annular depression, the other of said pair of annular expansions extending posteriorly from the approximate midpoint of said annular depression and having an increasing rate of annular expansion to define a truncated cone with a concave surface extending posteriorly from the approximate midpoint of said annular depression to the approximate apex of said other annular expansion; and
   (c) an inlet tube intersecting with said main tube for directing fluids into said main tube, said inlet tube having a diameter less than the diameter of said main tube.

2. The speculum as set forth in claim 1 wherein said proximal end includes a cylindrical section.

3. The speculum as set forth in claim 2 wherein said inlet tube intersects said cylindrical section.

4. The speculum as set forth in claim 1 wherein said proximal end includes a tapered section for circumsribingly receiving the waste discharge hose.

5. The speculum as set forth in claim 1 wherein said inlet tube intersects said main tube at an obtuse angle with respect to the proximal end of said main tube to direct a flow of fluid away from the distal end of said main tube.

6. The speculum as set forth in claim 1 including a thumb rest means extending radially from said main tube diametrically opposite the intersection between said main tube and said inlet tube.

7. A rectal speculum assembly for use with a colonic lavage machine, said assembly comprising:
   (a) a rectal speculum, said speculum including:
      (i) a hollow main tube, said main tube having a distal end for insertion into a patient's rectum and a proximal end for connection to a waste discharge hose,
      (ii) an inlet tube for directing fluids into said main tube, said inlet tube having a diameter less than the diameter of the main tube,
      (iii) an axially undulating exterior surface disposed about at least an axial length of said main tube and defining at least one annular depression for circumsribingly receiving and being gripped by the rectal sphincter muscle of a patient undergoing colonic lavage and one of a pair of annular expansions disposed on each side of said annular depression, one of said pair of annular expansions extending posteriorly from the anterior end of said main tube and having an increasing rate of annular expansion to define a truncated cone with a concave surface extending posteriorly from the anterior end of said main tube to the approximate apex of said one annular expansion, said one annular expansion having a decreasing rate of annular contraction posteriorly from the approximate apex to define a truncated cone with a concave surface extending posteriorly from the approximate apex of said one annular expansion to the approximate midpoint of said annular depression, the other of said pair of annular expansions extending posteriorly from the approximate midpoint of said annular depression and having an increasing rate of annular expansion to define a truncated cone with a concave surface extending posteriorly from the approximate midpoint of said annular depression to the approximate apex of said other annular expansion; and
   (b) an obturator removably positioned in said main tube of said speculum for facilitating insertion of said speculum into a patient's rectum, said obturator including;
      (i) an elongated rod extending through said main tube,
      (ii) a tapered cone portion formed at the distal end of said main tube, and
      (iii) a handle portion formed at the proximal end of said main tube to facilitate removal of said obturator from said speculum.

8. The assembly as set forth in claim 7 including a thumb rest for steadying said speculum in a patient's rectum during handling of the proximal end of said main tube.

9. The assembly as set forth in claim 8 wherein said thumb rest comprises a flange extending in diametrically opposed relationship to said inlet tube.

* * * * *

REEXAMINATION CERTIFICATE (2585th)
United States Patent [19]
Hawks

[11] B1 4,943,285
[45] Certificate Issued    May 23, 1995

[54] UNDULATING RECTAL SPECULUM

[75] Inventor: Robert A. Hawks, Glendale, Ariz.

[73] Assignee: Specialty Health Products, Inc., Phoenix, Ariz.

Reexamination Request:
No. 90/003,421, Apr. 28, 1994

Reexamination Certificate for:
Patent No.: 4,943,285
Issued: Jul. 24, 1990
Appl. No.: 289,566
Filed: Dec. 22, 1988

[51] Int. Cl.$^6$ .............................. A61M 31/00
[52] U.S. Cl. ........................ 604/275; 600/29
[58] Field of Search ............ 604/54, 164, 170, 275, 604/278, 279; 128/750; 600/29

[56] References Cited
U.S. PATENT DOCUMENTS

| | | | |
|---|---|---|---|
| 2,458,719 | 1/1949 | McCormick | 128/229 |
| 2,630,805 | 3/1953 | Brehm | 128/242 |
| 2,631,586 | 3/1953 | Reilly | 128/242 |
| 3,675,642 | 7/1972 | Lord | 128/1 |
| 3,842,834 | 10/1974 | Vass | 128/245 |
| 3,990,448 | 11/1976 | Mather et al. | 128/239 |
| 4,325,370 | 4/1982 | Young | 128/245 |
| 4,712,536 | 12/1987 | Hawks | 128/3 |
| 4,842,580 | 6/1989 | Ouelette | 604/30 |

FOREIGN PATENT DOCUMENTS 412656  7/1934  United Kingdom .

OTHER PUBLICATIONS

CM150 Hydrotherapy advertisement, E&R Diversified, (no date).

*Primary Examiner*—C. Fred Rosenbaum

[57] ABSTRACT

A rectal speculum for use in conjunction with colonic lavage has an axially undulating exterior surface for defining an annular depression to receive and be gripped by the rectal sphincter muscle upon insertion of the speculum.

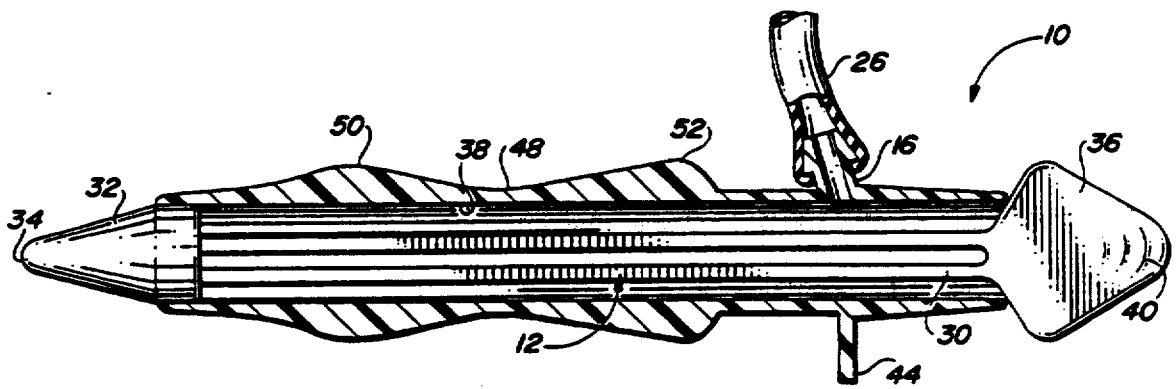

REEXAMINATION CERTIFICATE ISSUED UNDER 35 U.S.C. 307

NO AMENDMENTS HAVE BEEN MADE TO THE PATENT.

AS A RESULT OF REEXAMINATION, IT HAS BEEN DETERMINED THAT:

The patentability of claims 1-9 is confirmed.

* * * * *